United States Patent
Riquelme-Granada et al.

(10) Patent No.: US 12,367,223 B1
(45) Date of Patent: Jul. 22, 2025

(54) CALIBRATED LARGE LANGUAGE MODELS FOR MULTI-LABEL CLASSIFICATIONS

(71) Applicant: Distributed Analytics Solutions, Ltd., London (GB)

(72) Inventors: Nery Riquelme-Granada, London (GB); Khuong An Nguyen, London (GB); Stylianos Kapetanakis, London (GB); Zhiyuan Luo, London (GB)

(73) Assignee: Distributed Analytics Solutions, Ltd., London (GB)

( * ) Notice: Subject to any disclaimer, the term of this patent is extended or adjusted under 35 U.S.C. 154(b) by 0 days.

(21) Appl. No.: 18/951,159

(22) Filed: Nov. 18, 2024

(51) Int. Cl.
  *G06F 16/28* (2019.01)
  *G16H 50/70* (2018.01)

(52) U.S. Cl.
  CPC ........... *G06F 16/287* (2019.01); *G16H 50/70* (2018.01)

(58) Field of Classification Search
  CPC ....... G06F 16/287; G06F 40/50; G16H 50/70; G06N 20/40
  See application file for complete search history.

(56) References Cited

U.S. PATENT DOCUMENTS

| | | | |
|---|---|---|---|
| 12,032,919 B1* | 7/2024 | Szwabe | G06F 40/284 |
| 2024/0274286 A1* | 8/2024 | Chen | G16H 50/70 |
| 2024/0311094 A1* | 9/2024 | Auld | G06F 8/35 |
| 2024/0394541 A1* | 11/2024 | Cemgil | G06N 3/042 |
| 2025/0028905 A1* | 1/2025 | Atashbar | G06F 40/284 |
| 2025/0036604 A1* | 1/2025 | Manchanda | G06F 16/215 |

OTHER PUBLICATIONS

Yang et al., "Bayesian Reward Models for LLM Alignment," Jul. 3, 2024; 12 pages.
Nikitin et al., "Kernel Language Entropy: Fine-grained Uncertainty Quantification for LLMs from Semantic Similarities," May 30, 2024; 22 pages.
Kossen et al., "Semantic Entropy Probes: Robust and Cheap Hallucination Detection in LLMs," Jun. 22, 2024; 22 pages.
Ledger et al., "Detecting LLM Hallucinations Using Monte Carlo Simulations on Token Probabilities," TechRxiv. Jun. 12, 2024; 6 pages.
Ganda et al., "A Survey on Multi Label Classification," Recent Trends in Programming Languages. 2018; 5 pages.
Deng et al., "Efficient Detection of LLM-generated Texts with a Bayesian Surrogate Model," May 26, 2023; 14 pages.
Abburi et al., "Generative AI Text Classification using Ensemble LLM Approaches," Sep. 14, 2023; 8 pages.

* cited by examiner

*Primary Examiner* — Apu M Mofiz
*Assistant Examiner* — J Mitchell Curran
(74) *Attorney, Agent, or Firm* — Sterne, Kessler, Goldstein & Fox P.L.L.C.

(57) ABSTRACT

Aspects disclosed provide system and methods for providing reliability measures to outputs of large language models (LLMs). The system and methods do this by integrating Large Language Models (LLMs) in a multi-label classification setting, utilizing the Conformal Prediction (CP) framework. This approach ensures that the predictions made by the LLM are accompanied by mathematically guaranteed error bounds, enhancing the LLMs reliability and trustworthiness.

20 Claims, 6 Drawing Sheets

CALIBRATED LARGE LANGUAGE MODELS FOR MULTI-LABEL CLASSIFICATIONS

TECHNICAL FIELD

Aspects relate to generative artificial intelligence (AI), and specifically to large language models (LLMs).

BACKGROUND

LLMs have become pivotal in the Machine Learning (ML) domain due to their unprecedented predictive power and impressive linguistic capabilities. However, they exhibit significant limitations that hinder their deployment in high-risk and consequential tasks, such as healthcare diagnostics. One of the primary issues is the unreliability of LLMs when generating uncalibrated responses, especially in multi-label prediction scenarios. Multi-label prediction scenarios refer to situations where more than one classification may describe an input into the LLM. One reason for the unreliability is that LLMs do not provide any guarantees on their outputs, making them inherently unreliable for critical applications where accuracy and trustworthiness are paramount.

Additionally, LLMs are resource-intensive to train and expensive to store. Their complexity contributes to a lack of explainability of their outputs, making them challenging to understand and interpret. This opacity is further compounded by the fact that the data used for training LLMs is often hidden from users, raising concerns about biases and the validity of the models' knowledge base. These factors collectively pose significant barriers to the adoption of LLMs in domains that demand transparency, reliability, and efficiency.

Thus, solutions are needed to address the aforementioned problems.

SUMMARY

Aspects disclosed herein provide a system and methods for providing reliability measures to LLM outputs. The system and methods provides the reliability measures by integrating LLMs within a Conformal Prediction (CP) framework. CP is a rigorous statistical method that provides confidence levels for the outputs of ML models. This approach ensures that the predictions made by the LLM are accompanied by mathematically guaranteed error bounds, enhancing the LLMs reliability and trustworthiness.

By treating LLMs as a black box, the system and methods eliminates the need for LLM retraining or fine-tuning, thereby avoiding additional computational costs. The system and methods implements a theoretically-proven statistical procedure that calibrates the LLM's outputs without altering its internal mechanisms. Specifically, the system and methods use a calibration data—data that the LLM has not previously encountered but where there are known correct outcomes—to compute a conformity score for each instance in the calibration data. The conformity scores measure how well the LLM's predictions align with the actual known outcomes in the calibration data.

Based on a predefined error tolerance and the conformity scores, the system and methods calculates specific order statistics (a quantile score). The quantile score is then stored and used to evaluate new predictions regarding future data input into the LLM. For example, if future data is input into the LLM, the LLM can output a future plurality of classification values. The future plurality of classification values may be compared against to the quantile score. This comparison allows the system to determine a set of predictions that conform to the desired confidence level set forth by the error tolerance, effectively guaranteeing that the error rate does not exceed a specified error tolerance. This self-contained approach provides rigorous mathematical guarantees for each prediction made by the LLM. Thus, what is disclosed is a reliability layer built to compliment LLMs.

In aspects, the system can implement one or more computing devices to perform the aforementioned functionality. Starting with a calibration stage, in which a benchmark is set to assess and adjust the LLM's predictive confidence, the one or more computing devices can achieve the functionality by first inputting into a LLM, an instance of calibration data to be classified. A plurality of classification values classifying the instance may be received from the LLM, where each classification value of the plurality of classification values includes an associated probability representing a likelihood that each classification value is a valid output for the instance. A conformity score can then be computed for the instance. The conformity score for the instance can then be stored in an array for later use. The aforementioned procedure may be repeated for further instances of the calibration data. Once all the instances have conformity scores in the array, the system can compute a quantile score based on the array and a predefined error tolerance. The quantile score may be stored to be used as a cutoff for a future plurality of classification values associated with future data that is input into the LLM.

After the calibration stage, and in aspects, the system can use the quantile score to guarantee a certain level of confidence for future outputs of the LLM based on future data that is input into the LLM by the system. In aspects, the system can do this by inputting, into the LLM, the future data to be classified by the LLM. It should be noted that the future data and the calibration data should be from the same domain to be classified. In aspects, a future plurality of classification values classifying the future data may be received, where each future classification value of the future plurality of classification values includes an associated probability representing a likelihood that each future classification value is a valid output. The future plurality of classification values can then be ordered in descending order. A cutoff for the future plurality of classification values can then be determined based on the quantile score. In aspects, the system can output, to a graphical user interface (GUI), a subset of the future plurality of classification values from a highest probability to the cutoff, for display to a user.

The user may be any number of users. In the case where the calibration data and the future data are both related to healthcare data, the user may be, for example, a doctor that is using the system to predict with some confidence a diagnosis based on the healthcare data. The subset of future plurality of classification values may be predicted healthcare conditions or diseases. And the GUI may be an interface of an electronic health records management system. This is merely exemplary. The system and methods may be expanded to other domains as will be understood by a person of ordinary skill in the art (POSA) by reading this disclosure.

In aspects, in order to improve the system, the quantile score may be re-computed based on updated calibration data. This may be done at predetermined intervals to incorporate any new calibration data. In this way, the system may be tuned to provide better reliability/confidence metrics over time if better calibration data is available. This may be done without the computationally expensive task of having to update or retune the LLM itself.

Certain aspects have other steps or elements in addition to or in place of those mentioned above. The steps or elements will become apparent to a POSA from a reading of the following detailed description when taken with reference to the accompanying drawings.

BRIEF DESCRIPTION OF THE DRAWINGS

The accompanying drawings, which are incorporated herein and form a part of the specification, illustrate aspects of the present disclosure and, together with the description, further serve to explain the principles of the disclosure and to enable a POSA to make and use the aspects.

DETAILED DESCRIPTION

Figure 1:
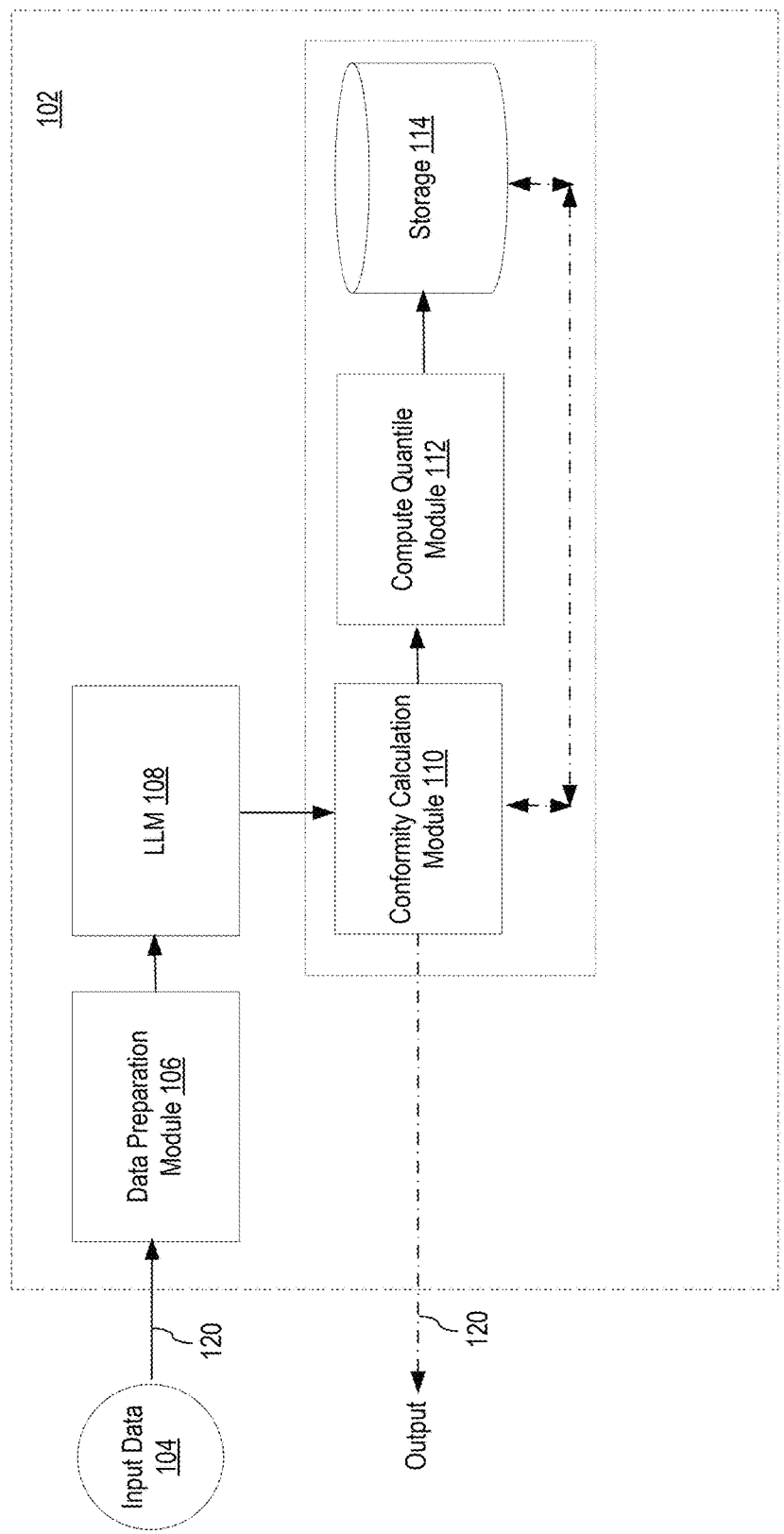
FIG. 1 is an example system for providing reliability measures to LLM outputs according to aspects.

Aspects disclosed herein provide a system and methods for providing reliability measures to LLM outputs. The system and methods provides an enhancement to existing LLMs because it attaches a reliability layer to existing LLMs. The reliability layer guarantees a baseline level of certainty/confidence in the LLM's outputs.

The system and methods is distinct over existing solutions in several aspects. First, the system and methods does not rely on any particular data distribution to provide its guarantees unlike some current approaches to the problem. For example, current solutions addressing LLM reliability commonly use Bayesian approaches to predict reliability. However, these approaches require knowledge about the data distribution and impose heavy assumptions on the prediction tasks. Incorrect assumptions can lead to invalid probability estimates. The system disclosed, however, operates in a distribution-free manner, meaning it does not rely on any assumptions about how the data is generated. This ensures that the confidence levels provided are valid regardless of the underlying data distribution.

Second, existing methods estimate reliability using external sources such as expert advice or semantic entropy. Example approaches using this approach are, for example, retrieval-augmented generation (RAG) systems. These approaches, however, cannot guarantee trustworthiness, as they depend on factors outside the model's control. In contrast, the disclosed system and methods is self-contained and provides rigorous error bounds for every statement made by the LLM. By relying solely on the model's outputs and a calibration dataset, the system eliminates the need for external inputs.

Third, existing methods often require re-training LLM models or incorporating human-in-the-loop techniques, which are computationally intensive and time-consuming. Ensemble methods, for example, estimate uncertainty by aggregating predictions from multiple models. The system disclosed, however, is computationally efficient because it relies on a single LLM and avoids re-training. This simplicity makes the disclosed approach more elegant and practical for real-world applications.

Fourth, existing methods take token probabilities at face value, which may be misleading due to the overconfidence of LLMs. The system does not use these probabilities directly. Instead, the system calibrates them to make them reliable, ensuring that the predicted confidence levels accurately reflect the true likelihood of each outcome.

Fifth, many critical tasks, such as medical diagnosis, require multi-label predictions where multiple conditions or labels may be present simultaneously. The system disclosed is particularly suited for these scenarios, as it can provide statistically valid confidence levels for each label in a multi-label setting. This capability addresses a significant need in fields where complex, concurrent predictions are essential.

The following aspects are described in sufficient detail to enable those skilled in the art to make and use the disclosure. It is to be understood that other aspects are evident based on the present disclosure, and that system, process, or mechanical changes may be made without departing from the scope of aspects of the present disclosure.

In the following description, numerous specific details are given to provide a thorough understanding of the disclosure. However, it will be apparent that the disclosure may be practiced without these specific details. In order to avoid obscuring an aspect of the present disclosure, some well-known circuits, system configurations, architectures, and process steps are not disclosed in detail.

The drawings showing aspects of the system are semi-diagrammatic, and not to scale. Some of the dimensions are for the clarity of presentation and are shown exaggerated in the drawing figures. Similarly, although the views in the drawings are for ease of description and generally show similar orientations, this depiction in the figures is arbitrary for the most part. Generally, the disclosure may be operated in any orientation.

The term "module" or "unit" referred to herein may include software, hardware, or a combination thereof in an aspect of the present disclosure in accordance with the context in which the term is used. For example, the software may be machine code, firmware, embedded code, or application software. Also, for example, the hardware may be circuitry, a processor, a special purpose computer, an integrated circuit, integrated circuit cores, or a combination thereof. Further, if a module or unit is written in the system or apparatus claims section below, the module or unit is deemed to include hardware circuitry for the purposes and the scope of the system or apparatus claims.

The modules or units in the following description of the aspects may be coupled to one another as described or as shown. The coupling may be direct or indirect, without or with intervening items between coupled modules or units. The coupling may be by physical contact or by communication between modules or units.

System Overview and Function

FIG. 1 is an example system 100 for providing reliability measures to LLM 108 outputs according to aspects. In aspects, the system 100 may be implemented on one or more computing devices, including server infrastructure of a company, a cloud services provider, etc. For example, the system 100 may be housed in a cloud-computing environment 102. The cloud-computing environment 102 can include server infrastructure. The cloud-computing environment 102 may be a public or private cloud service. A private cloud refers to a cloud environment similar to a public cloud with the exception that it is operated solely for a single organization.

In aspects, the cloud-computing environment 102 can comprise a variety of centralized or decentralized computing devices. For example, the cloud-computing environment 102 may include a mobile device, a laptop computer, a desktop computer, grid-computing resources, a virtualized computing resource, cloud-computing resources, peer-to-peer distributed computing devices, a server, a server farm, or a combination thereof. The cloud-computing environment 102 may be centralized in a single room, distributed across different rooms, distributed across different geographic locations, or embedded within a network 120.

In aspects, and as shown in FIG. 1, the computing devices of the cloud-computing environment 102 may have various software modules stored thereon to enable the functions of the system 100. In aspects, these modules can include a data preparation module 106, a LLM 108, a conformity calculation module 110, and a compute quantile module 112. Each of these modules will be discussed in detail below.

The network 120 refers to a telecommunications network, such as a wired or wireless network. The network 120 can span and represent a variety of networks and network topologies. For example, the network 120 can include wireless communication, wired communication, optical communication, ultrasonic communication, or a combination thereof. For example, satellite communication, cellular communication, Bluetooth, Near Field Communications (NFC), Infrared Data Association standard (IrDA), wireless fidelity (WiFi), and worldwide interoperability for microwave access (WiMAX) are examples of wireless communication that may be included in the network 120. Cable, Ethernet, digital subscriber line (DSL), fiber optic lines, fiber to the home (FTTH), and plain old telephone service (POTS) are examples of wired communication that may be included in the network 120. Further, the network 120 can traverse a number of topologies and distances. For example, the network 120 can include a direct connection, personal area network (PAN), local area network (LAN), metropolitan area network (MAN), wide area network (WAN), or a combination thereof.

In aspects, and as shown in FIG. 1, the system 100 can first perform a calibration procedure to initialize the system 100. The calibration procedure refers to a process by which the system 100 can set a benchmark to assess and adjust the LLM's 108 predictive confidence. The system 100 may begin the calibration procedure by first receiving input data 104 from a data source. The data source may be, for example, a computer or database storing the input data 104. The input data 104 refers to data from a target domain for which the LLM 108 will be making predictions. For example, if the target domain is medical diagnostics, the input data 104 may be, for example, chest radiographs or x-rays covering a range of conditions the LLM 108 is expected to identify from the data. This is exemplary, and any target domain and data set may be adapted to use the system 100 as will be recognized by a POSA reading this disclosure.

During the calibration procedure, the input data 104 will be referred to as calibration data. For the calibration procedure to work as intended, it is important and assumed that the calibration data has not been previously used to train or fine-tune the LLM 108. This is to prevent any data leakage or bias of the LLM 108 when classifying the calibration data initially. It is also important that the calibration data be pre-labeled with known and correct labels. The LLM 108 will be asked to predict the correct labels for each instance of the calibration data, without actually knowing of the known and correct labels itself. Thus, the calibration procedure will determine how well the LLM's 108 output matches to known and correct outcomes.

In aspects, an instance of the calibration data may be transmitted to, and received by, the data preparation module 106. The data preparation module 106 refers to a software program and/or class of software libraries that when executed by one or more computing devices, performs functions to shape the instance into a desired format to be input into the LLM 108. For example, to match the input format expected by the LLM 108, the data preparation module 106 can execute code to perform some preprocessing steps. If the instance is an image, such as a chest radiograph or x-ray, the preprocessing steps can include such things as resizing images, normalizing pixel values, and formatting the data according to the LLM's 108 requirements. If the instance is textual, the preprocessing steps may involve tokenization, encoding, and removing any irrelevant or sensitive information prior to putting the instance into the LLM 108. In aspects, the data preparation module 106 can also indicate what format the output of the LLM 108 should take. This may be, for example, providing a template format of what the outputs should look like. In this way, the LLM's 108 outputs may be conformed to an expected or desired format. Proper data preparation by the data preparation module 106 ensures that the LLM 108 can process instances of the calibration data effectively, leading to accurate computation of conformity scores, as will be discussed later in this disclosure.

In aspects, once formatted by the data preparation module 106, the instance may be input into the LLM 108. The LLM 108 can process the instance and generate an output based on the instance. In aspects, and taking the example of medical diagnostics, the output may be a plurality of classification values classifying the instance. The plurality of classification values may be, for example, predicted diagnoses of diseases/medical conditions that may be predicted and/or deduced from the instance. For example, if the instance is a chest radiograph or x-ray, the predicted diagnoses may be pneumonia, tuberculosis, emphysema, lung cancer, chronic obstructive pulmonary disease (COPD), pulmonary fibrosis, sarcoidosis, etc. In aspects, each classification value of the plurality of classification values can also include an associated probability/confidence score representing a likelihood that each classification value is a valid output. For example, for a chest x-ray, the LLM 108 can output a set of diagnoses indicating what diseases/medical conditions the LLM 108 believes the chest x-ray shows (pneumonia, tuberculosis, emphysema, etc.), accompanied by a probability score (either represented as a percentage or a softmax function probability) of how certain the LLM 108 is that its predicted disease/medical condition is the correct prediction.

In aspects, the plurality of classification values can then be transmitted to, and received by, the conformity calculation module 110. The conformity calculation module 110 refers to a software program and/or class of software libraries that when executed by one or more computing devices, performs functions to compute a conformity score for the instance. The conformity score refers to a quantified value representing how well the LLM's 108 prediction aligns with the true diagnosis shown in the instance of calibration data. In aspects, the conformity score may be computed by sorting each classification value in descending order, and starting from a highest probability outcome, adding each associated probability for all known valid outputs of the instance. In aspects, once the conformity score for the instance is determined, it may be stored in an array. The array can be represented as "a" throughout this disclosure.

Figure 2:
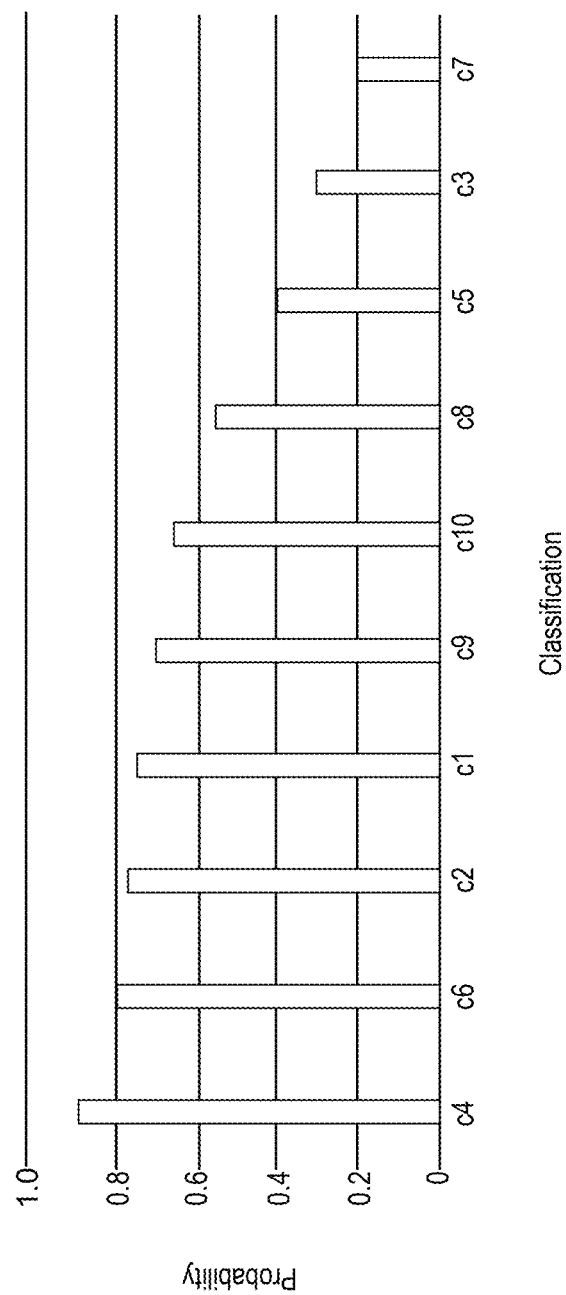
FIG. 2 shows how a plurality of classification values is ordered by the system according to aspects.

FIG. 2 shows how a plurality of classification values is ordered by the system 100 according to aspects. In FIG. 2, the plurality of classification values is shown on the x-axis and are indicated by {c1, c2 . . . , c10}. The probability/confidence score associated with each classification value is shown on the y-axis and are in the range of [0, 1] indicating a probability from 0% to 100%.

In aspects, and for further instances of calibration data, the above described procedure may be performed to obtain a collection of conformity scores across all instances of the calibration data. This collection provides the statistical basis for assessing the LLM's 108 predictive behavior.

In aspects, once the array of conformity scores is obtained, the array may be transmitted to, and received by, the compute quantile module 112. The compute quantile module 112 refers to a software program and/or class of software libraries that when executed by one or more computing devices, performs functions to compute a quantile score based on the array and a predefined error tolerance. The quantile score refers to a quantifiable value that serves as a threshold or cutoff value that determines the level of confidence required by the LLM's 108 future predictions to be considered reliable. The predefined error tolerance refers to a level of error that is acceptable for the system 100 when predicting what classifications are the correct ones. The error tolerance can be an opposite way of thinking of the system's 100 confidence. For example, if we set the error to 10%, then the confidence of the prediction sets will be 90%; if the error is set to 40%, then the confidence of the prediction sets will be 60%. In aspects, both the error tolerance and the confidence will always be a real number in the range of [0, 1], representing the percentage of error tolerance and confidence desired for the system 100. The compute quantile module 112 can compute the quantile score using any number of known methods. For example, if the software implementing the compute quantile module 112 is implemented using the Python computer programming language, the function "np.quantile($\alpha,\epsilon$)" may be used to compute the quantile score, where $\alpha$ is the array, and $\epsilon$ is the error tolerance. The output of the function will be a numerical value.

In aspects, the quantile score may be stored and used as a cutoff for a future plurality of classification values associated with future data that is input into the LLM 108. For example, and as shown in FIG. 1, storage 114 can store the quantile score. This step forms the conclusion of the calibration procedure. How the quantile score will be used on future data will now be described.

In aspects, once the system 100 is calibrated, it may be used on future data to be classified by the LLM 108. As previously indicated, the future data should be in the same domain as the calibration data. Taking the instance where the calibration data was a chest radiograph or x-ray, the future data would also have to be a chest radiograph or x-ray. In aspects, the system 100 can receive from a data source the future data as its input data 104. In aspects, the same preprocessing described with respect to the calibration procedure may be performed on the future data by the data preparation module 106. Once the future data is preprocessed, it is input into the LLM 108 to be classified. The LLM 108 can generate a future plurality of classification values classifying the future data. Similar to what was described in the calibration procedure, each future classification value of the future plurality of classification values can include an associated probability representing a likelihood that each future classification value is a valid output.

Figure 3:
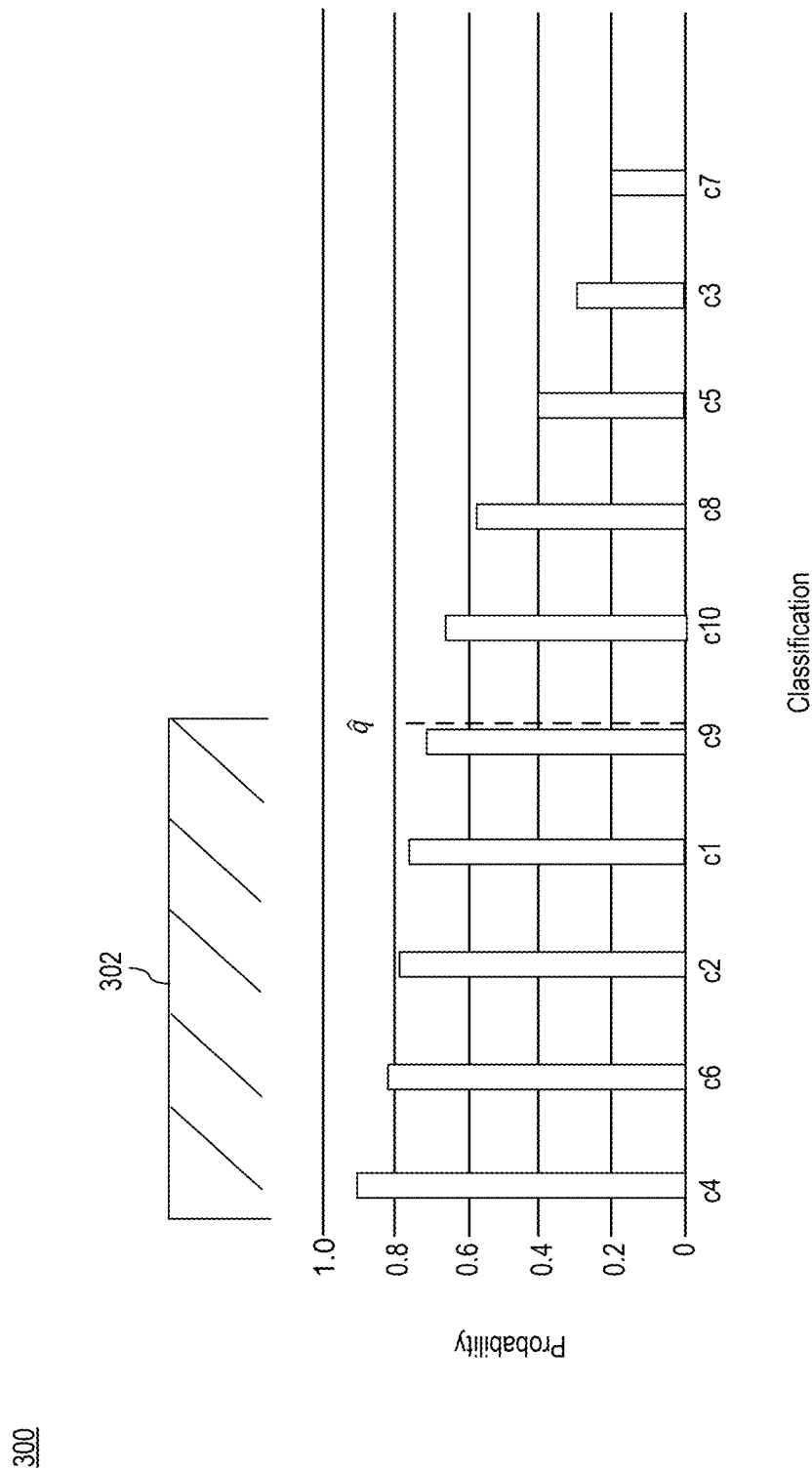
FIG. 3 shows how a subset of a future plurality of classification values is obtained based on a cutoff according to aspects.

In aspects, once the plurality of classification values is obtained, the values may be transmitted to, and received by, the conformity calculation module 110. This time, rather than compute conformity scores, the conformity calculation module 110 can simply order the future plurality of classification values in descending order. Once ordered, the conformity calculation module 110 can determine a cutoff for the future plurality of classification values based on the stored quantile score, which it can look up and obtain from the storage 114. In aspects, the cutoff can discard any of the future classification values of the future plurality of classification values that fall below the value of the cutoff. In this way, a prediction set is obtained based on a subset of the future plurality of classification values that the system 100 can determine is within the error tolerance desired. FIG. 3 shows how a subset of a future plurality of classification values is obtained based on the cutoff according to aspects. In FIG. 3, the quantile score is shown by q, and the future plurality of classification values within the region shown in 302 are the subset of the future plurality of classification values that the system 100 determines is within the error tolerance desired.

In aspects, this subset of the future plurality of classification values may be output to a GUI for display to a user. As previously indicated, and taking the example where the future data relates to healthcare diagnostics, the GUI may be that of an electronics health record management system displaying the predicted diagnoses based on the data, and the user may be a doctor.

In order to improve the system 100, from time to time and at predetermined intervals, the quantile score may be re-computed using updated calibration data in the same manner as was described with respect to the calibration procedure. As previously indicated, this is a way of updating the confidence levels of the system 100 in a computationally efficient way when better calibration data is available.

The functions of the system 100 may be performed by the modules or units of the server infrastructure of the system 100, for example the computing devices of the cloud-computing environment 102. The modules or units may be implemented as instructions stored on a non-transitory computer readable medium to be executed by one or more computing units such as a processor, a special purpose computer, an integrated circuit, integrated circuit cores, or a combination thereof. The non-transitory computer readable medium may be implemented with any number of memory units, such as a volatile memory, a nonvolatile memory, an internal memory, an external memory, or a combination thereof. The non-transitory computer readable medium may be integrated as a part of the system 100, or installed as a removable portion of the system 100.

Methods of Operation

Figure 4:
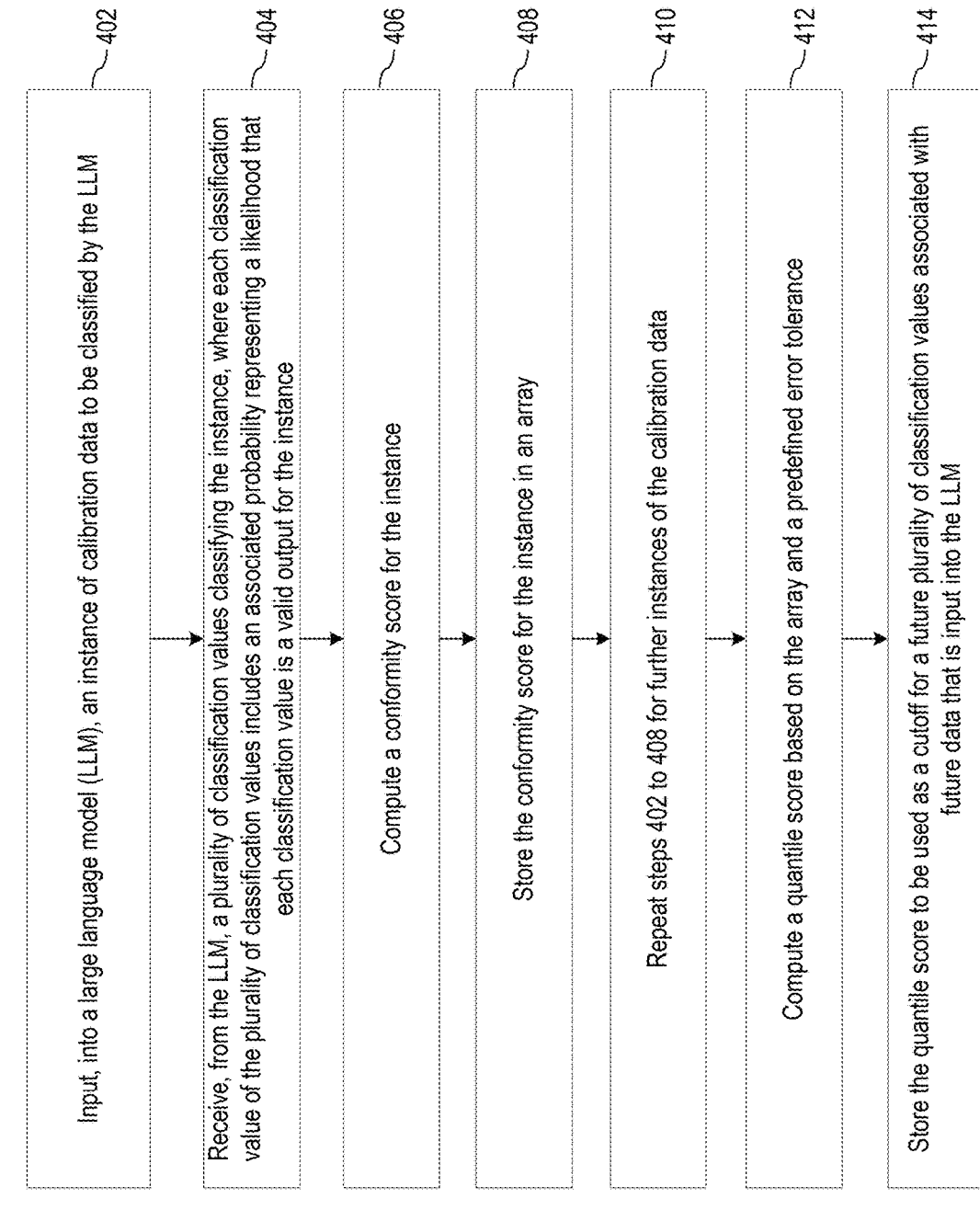
FIG. 4 is an example method of operating the system according to aspects.

FIG. 4 is an example method 400 of operating the system 100 according to aspects. Method 400 may be implemented on computing devices, for example the computing devices of the cloud-computing environment 102. Method 400 reflects the steps of the calibration procedure described above.

In aspects, method 400 may begin by inputting into a LLM 108, an instance of calibration data to be classified, as shown in step 402. A plurality of classification values classifying the instance may be received from the LLM 108, where each classification value of the plurality of classification values includes an associated probability representing a likelihood that each classification value is a valid output for the instance, as shown in step 404. A conformity score can then be computed for the instance, as shown in step 406. The conformity score can be computed by the conformity calculation module 110. The conformity score for the instance can then be stored in an array for later use, as shown in step 408. The aforementioned procedure may be repeated for further instances of the calibration data, as shown in step 410. Once all the instances of the calibration data have conformity scores in the array, the system 100 can compute a quantile score based on the array and a predefined error tolerance, as shown in step 412. This can be done by the compute quantile module. The quantile score may be stored to be used as a cutoff for a future plurality of classification values associated with future data that is input into the LLM 108, as shown in step 414. For example, storage 114 can store the quantile score.

Figure 5:
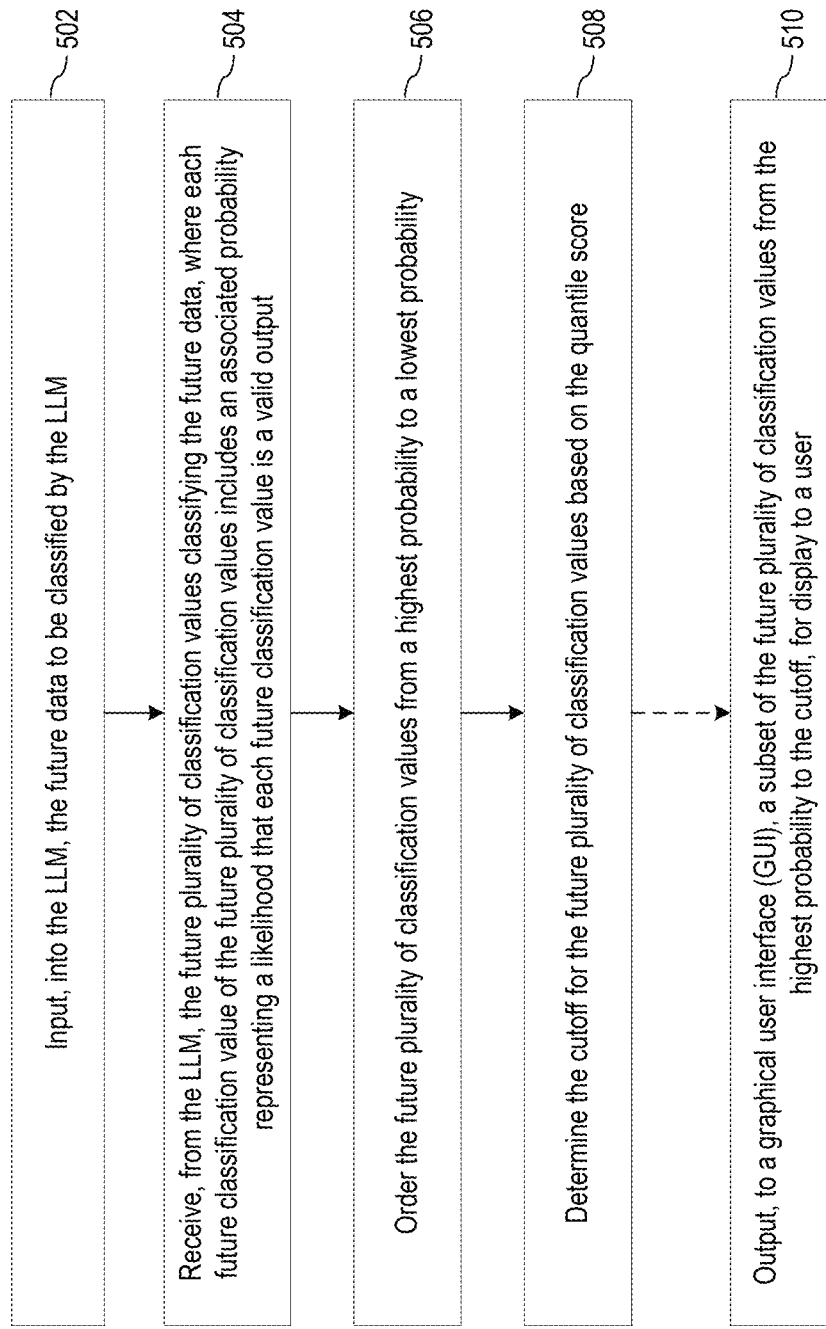
FIG. 5 is a further example method of operating the system according to aspects.

FIG. 5 is a further example method 500 of operating the system 100 according to aspects. Method 500 may be implemented on computing devices, for example the computing devices of the cloud-computing environment 102. Method 500 reflects the steps after the calibration procedure described above.

In aspects, method 500 may begin by inputting, into the LLM 108, the future data to be classified by the LLM 108, as shown in step 502. A future plurality of classification values classifying the future data may be received from the LLM 108, where each future classification value of the future plurality of classification values includes an associated probability representing a likelihood that each future classification value is a valid output, as shown in step 504. The future plurality of classification values can then be ordered in descending order, as shown in step 506. This ordering can be done by the conformity calculation module 110. A cutoff for the future plurality of classification values can then be determined based on the quantile score, as shown in step 508. Based on the cutoff, a set of the future plurality of classification values can be obtained and can be displayed to a user, or otherwise used in further downstream processing. In aspects, the system 100 can optionally output, to a GUI, the subset of the future plurality of classification values from a highest probability to the cutoff, for display to a user, as shown in step 510.

The operations of methods 400 and 500 are performed, for example, by system 100, in accordance with aspects described above. The functions described may be performed according to and consistent with FIGS. 1-3, and by the data preparation module 106, the LLM 108, the conformity calculation module 110, and the compute quantile module 112, or their equivalents as described above. Such modules may be combined in various ways or manners to perform the functions described with respect to methods 400 and 500.

Components of the System

Figure 6:
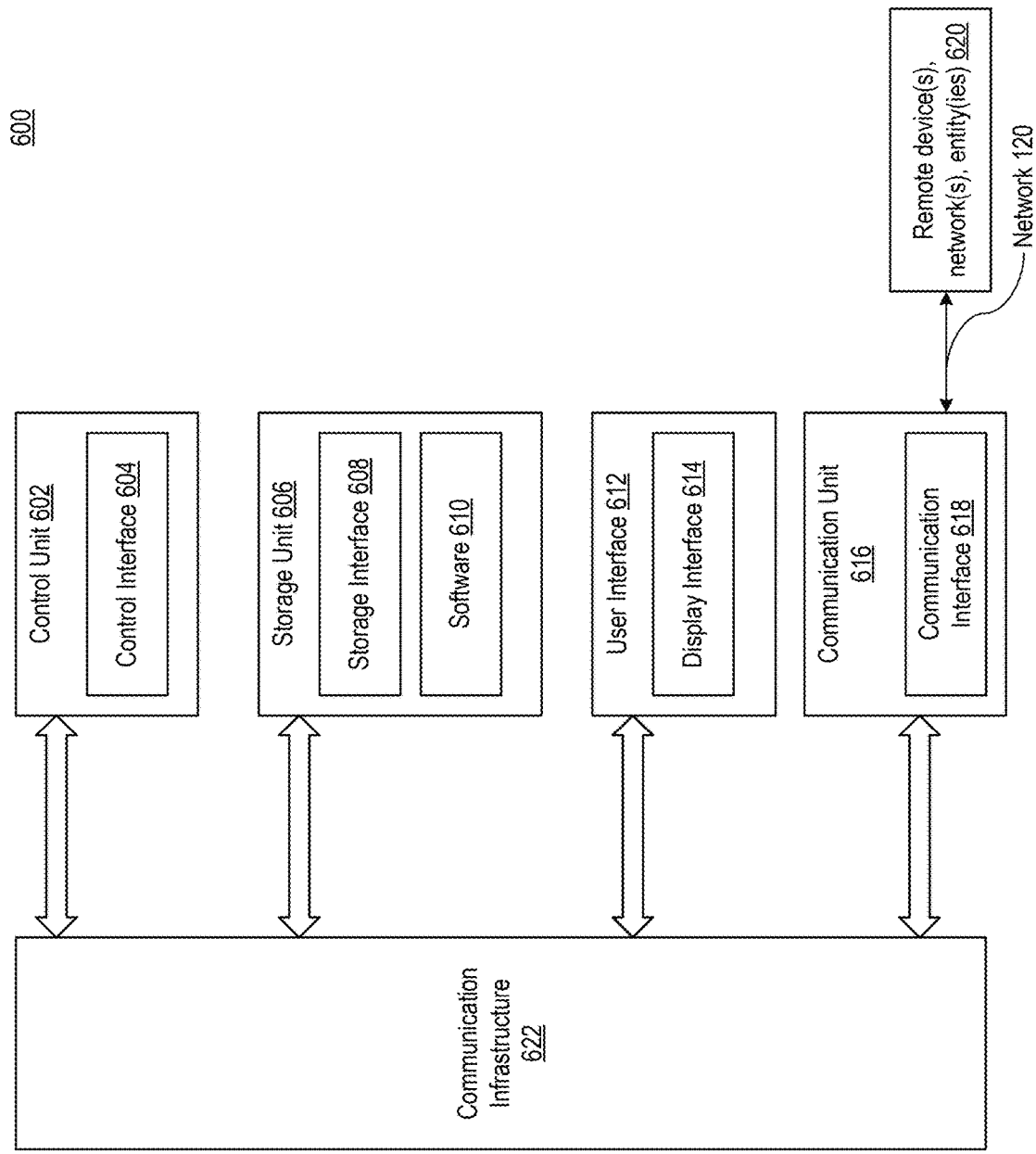
FIG. 6 is an example architecture of the components that may be used to implement the computing devices of the system according to aspects.

FIG. 6 is an example architecture 600 of the components that may be used to implement the computing devices of the system 100 according to aspects. The components may be implemented on any of the devices of the system 100, for example the computing devices of the cloud-computing environment 102. In aspects, the components may include a control unit 602, a storage unit 606, a communication unit 616, and a user interface 612. The control unit 602 may include a control interface 604. The control unit 602 may execute software 610 to provide some or all of the intelligence of system 100. The control unit 602 may be implemented in a number of different ways. For example, the control unit 602 may be a processor (e.g., central processing unit (CPU) or a graphics processing unit (GPU)), an application specific integrated circuit (ASIC), an embedded processor, a microprocessor, a hardware control logic, a hardware finite state machine (FSM), a digital signal processor (DSP), a field programmable gate array (FPGA), or a combination thereof.

The control interface 604 may be used for communication between the control unit 602 and other functional units or devices of system 100. The control interface 604 may also be used for communication that is external to the functional units or devices of system 100. The control interface 604 may receive information from the functional units or devices of system 100, or from remote devices 620, or may transmit information to the functional units or devices of system 100, or to remote devices 620. The remote devices 620 refer to devices external to system 100, such as any interfaces or computers used provide the input data 104 into the system 100.

The control interface 604 may be implemented in different ways and may include different implementations depending on which functional units or devices of system 100 or remote devices 620 are being interfaced with the control unit 602. For example, the control interface 604 may be implemented with integrated circuits, optical circuitry, waveguides, wireless circuitry, wireline circuitry to attach to a bus, an application programming interface (API), or a combination thereof. The control interface 604 may be connected to a communication infrastructure 622, such as a bus, to interface with the functional units or devices of system 100 or remote devices 620.

The storage unit 606 may store the software 610. For illustrative purposes, the storage unit 606 is shown as a single element, although it is understood that the storage unit 606 may be a distribution of storage elements. Also for illustrative purposes, the storage unit 606 is shown as a single hierarchy storage system, although it is understood that the storage unit 606 may be in a different configuration. For example, the storage unit 606 may be formed with different storage technologies forming a memory hierarchical system including different levels of caching, main memory, rotating media, or off-line storage. The storage unit 606 may be a volatile memory, a nonvolatile memory, an internal memory, an external memory, or a combination thereof. For example, the storage unit 606 may be a non-volatile storage such as nonvolatile random access memory (NVRAM), Flash memory, disk storage, or a volatile storage such as static random access memory (SRAM) or dynamic random access memory (DRAM).

The storage unit 606 may include a storage interface 608. The storage interface 608 may be used for communication between the storage unit 606 and other functional units or devices of system 100. The storage interface 608 may also be used for communication that is external to system 100. The storage interface 608 may receive information from the other functional units or devices of system 100 or from remote devices 620, or may transmit information to the other functional units or devices of system 100 or to remote devices 620. The storage interface 608 may include different implementations depending on which functional units or devices of system 100 or remote devices 620 are being interfaced with the storage unit 606. The storage interface 608 may be implemented with technologies and techniques similar to the implementation of the control interface 604.

The communication unit 616 may enable communication to devices, components, modules, or units of system 100 or to remote devices 620. For example, the communication unit 616 may permit the system 100 to communicate between the modules of the cloud-computing environment 102. The communication unit 616 may further permit the devices of system 100 to communicate with remote devices 620 such as an attachment, a peripheral device, or a combination thereof, through the network 120, or to data sources providing the input data 104 into the system 100.

As previously indicated, the network 120 may span and represent a variety of networks and network topologies. For example, the network 120 may include wireless communication, wired communication, optical communication, ultrasonic communication, or a combination thereof. For example, satellite communication, cellular communication, Bluetooth, Infrared Data Association standard (IrDA), wireless fidelity (WiFi), and worldwide interoperability for microwave access (WiMAX) are examples of wireless communication that may be included in the network 120. Cable, Ethernet, digital subscriber line (DSL), fiber optic lines, fiber to the home (FTTH), and plain old telephone service (POTS) are examples of wired communication that may be included in the network 120. Further, the network 120 may traverse a number of network topologies and distances. For example, the network 120 may include direct connection, personal area network (PAN), local area network (LAN), metropolitan area network (MAN), wide area network (WAN), or a combination thereof.

The communication unit 616 may also function as a communication hub allowing system 100 to function as part of the network 120 and not be limited to be an end point or terminal unit to the network 120. The communication unit 616 may include active and passive components, such as microelectronics, communications circuitry, Radio Frequency (RF) circuitry, or an antenna, for interaction with the network 120.

The communication unit 616 may include a communication interface 618. The communication interface 618 may be used for communication between the communication unit 616 and other functional units or devices of system 100 or to remote devices 620. The communication interface 618 may receive information from the other functional units or devices of system 100, or from remote devices 620, or may transmit information to the other functional units or devices of the system 100 or to remote devices 620. The communication interface 618 may include different implementations depending on which functional units or devices are being interfaced with the communication unit 616. The communication interface 618 may be implemented with technologies and techniques similar to the implementation of the control interface 604.

The user interface 612 may present information generated by system 100. In aspects, the user interface 612 allows a user to interface with the devices of system 100 or remote devices 620. The user interface 612 may include an input device and an output device. Examples of the input device of the user interface 612 may include a keypad, buttons, switches, touchpads, soft-keys, a keyboard, a mouse, or any combination thereof to provide data and communication inputs. Examples of the output device may include a display interface 614. The control unit 602 may operate the user interface 612 to present information generated by system 100, for example, the subset of future plurality of classification values. The control unit 602 may also execute the software 610 to present information generated by system 100, or to control other functional units of system 100. The display interface 614 may be any graphical user interface such as a display, a projector, a video screen, or any combination thereof.

The above detailed description and aspects of the disclosed system 100 are not intended to be exhaustive or to limit the disclosed system 100 to the precise form disclosed above. While specific examples for system 100 are described above for illustrative purposes, various equivalent modifications are possible within the scope of the disclosed system 100, as a POSA will recognize. For example, while processes and methods are presented in a given order, alternative implementations may perform routines having steps, or employ systems having processes or methods, in a different order, and some processes or methods may be deleted, moved, added, subdivided, combined, or modified to provide alternative or sub-combinations. Each of these processes or methods may be implemented in a variety of different ways. Also, while processes or methods are at times shown as being performed in series, these processes or blocks may instead be performed or implemented in parallel, or may be performed at different times.

The resulting methods and system 100 is cost-effective, highly versatile, and accurate, and may be implemented by adapting components for ready, efficient, and economical manufacturing, application, and utilization. Another important aspect of aspects of the present disclosure is that it valuably supports and services the historical trend of reducing costs, simplifying systems, and/or increasing performance.

These and other valuable aspects of the present disclosure consequently further the state of the technology to at least the next level. While the disclosed aspects have been described as the best mode of implementing system 100, it is to be understood that many alternatives, modifications, and variations will be apparent to those skilled in the art in light of the descriptions herein. Accordingly, it is intended to embrace all such alternatives, modifications, and variations that fall within the scope of the included claims. All matters set forth herein or shown in the accompanying drawings are to be interpreted in an illustrative and non-limiting sense. Accordingly, the scope of the disclosure should be determined not by the aspects illustrated, but by the appended claims and their equivalents.

What is claimed is:

1. A computer-implemented method comprising:
    (a) inputting, by one or more computing devices and into a large language model (LLM), an instance of calibration data to be classified by the LLM, wherein:
        the calibration data is data that the LLM has not previously encountered, and
        the calibration data is pre-labeled with known and correct labels classifying valid outputs based on the calibration data;
    (b) receiving, by the one or more computing devices and from the LLM, a plurality of classification values classifying the instance, wherein each classification value of the plurality of classification values includes an associated probability representing a likelihood that each classification value is a valid output for the instance;
    (c) computing, by the one or more computing devices, a conformity score measuring how well the LLM output aligns with the known and correct labels of the calibration data for the instance;
    (d) storing, by the one or more computing devices, the conformity score for the instance in an array;
    (e) repeating, by the one or more computing devices, (a)-(d) for further instances of the calibration data;
    (f) computing, by the one or more computing devices, a quantile score based on the array and a predefined error tolerance; and
    (g) storing, by the one or more computing devices, the quantile score to be used as a cutoff for a future plurality of classification values associated with future data that is input into the LLM.

2. The method of claim 1, further comprising, computing, by the one or more computing devices, the conformity score by:
sorting each classification value in descending order; and
starting from a highest probability outcome, adding each associated probability for all known valid outputs.

3. The method of claim 1, wherein the calibration data relates to healthcare data.

4. The method of claim 2, wherein the plurality of classification values relates to potential diagnoses of health conditions based on the healthcare data.

5. The method of claim 1, further comprising:
inputting, by the one or more computing devices and into the LLM, the future data to be classified by the LLM;
receiving, by the one or more computing devices and from the LLM, the future plurality of classification values classifying the future data, wherein each future classification value of the future plurality of classification values includes an associated probability representing a likelihood that each future classification value is a valid output;
ordering, by the one or more computing devices, the future plurality of classification values in descending order; and
determining, by the one or more computing devices, the cutoff for the future plurality of classification values based on the quantile score.

6. The method of claim 5, further comprising outputting, by the one or more computing devices and to a graphical user interface (GUI), a subset of the future plurality of classification values from a highest probability to the cutoff, for display to a user.

7. The method of claim 1, further comprising, re-computing, by the one or more computing devices, the quantile score at predetermined intervals using updated calibration data.

8. A non-transitory computer readable medium including instructions, that when executed by one or more processors of a computing system, cause the computing system to perform operations comprising:
(a) inputting, into a large language model (LLM), an instance of calibration data to be classified by the LLM, wherein:
the calibration data is data that the LLM has not previously encountered, and
the calibration data is pre-labeled with known and correct labels classifying valid outputs based on the calibration data;
(b) receiving, from the LLM, a plurality of classification values classifying the instance, wherein each classification value of the plurality of classification values includes an associated probability representing a likelihood that each classification value is a valid output for the instance;
(c) computing a conformity score measuring how well the LLM output aligns with the known and correct labels of the calibration data for the instance;
(d) storing the conformity score for the instance in an array;
(e) repeating (a)-(d) for further instances of the calibration data;
(f) computing a quantile score based on the array and a predefined error tolerance; and
(g) storing the quantile score to be used as a cutoff for a future plurality of classification values associated with future data that is input into the LLM.

9. The non-transitory computer readable medium of claim 8, wherein the operations further comprise, computing the conformity score by:
sorting each classification value in descending order; and
starting from a highest probability outcome, adding each associated probability for all known valid outputs.

10. The non-transitory computer readable medium of claim 8, wherein the calibration data relates to healthcare data.

11. The non-transitory computer readable medium of claim 10, wherein the plurality of classification values relates to potential diagnoses of health conditions based on the healthcare data.

12. The non-transitory computer readable medium of claim 8, wherein the operations further comprise:
inputting, into the LLM, the future data to be classified by the LLM;
receiving, from the LLM, the future plurality of classification values classifying the future data, wherein each future classification value of the future plurality of classification values includes an associated probability representing a likelihood that each future classification value is a valid output;
ordering the future plurality of classification values in descending order; and
determining the cutoff for the future plurality of classification values based on the quantile score.

13. The non-transitory computer readable medium of claim 12, wherein the operations further comprise outputting, to a graphical user interface (GUI), a subset of the future plurality of classification values from a highest probability to the cutoff, for display to a user.

14. The non-transitory computer readable medium of claim 8, wherein the operations further comprise, re-computing the quantile score at predetermined intervals using updated calibration data.

15. A computing system comprising:
a memory;
one or more processors, coupled to the memory and configured to:
(a) input, into a large language model (LLM), an instance of calibration data to be classified by the LLM, wherein:
the calibration data is data that the LLM has not previously encountered, and
the calibration data is pre-labeled with known and correct labels classifying valid outputs based on the calibration data;
(b) receive, from the LLM, a plurality of classification values classifying the instance, wherein each classification value of the plurality of classification values includes an associated probability representing a likelihood that each classification value is a valid output for the instance;
(c) compute a conformity score measuring how well the LLM output aligns with the known and correct labels of the calibration data for the instance;
(d) store the conformity score for the instance in an array;
(e) repeat (a)-(d) for further instances of the calibration data;
(f) compute a quantile score based on the array and a predefined error tolerance; and (g) store the quantile score to be used as a cutoff for a future plurality of classification values associated with future data that is input into the LLM.

16. The computing system of claim 15, wherein the one or more processors are further configured to, compute the conformity score by:
sorting each classification value in descending order; and
starting from a highest probability outcome, adding each associated probability for all known valid outputs.

17. The computing system of claim 15, wherein the calibration data relates to healthcare data.

18. The computing system of claim 17, wherein the plurality of classification values relates to potential diagnoses of health conditions based on the healthcare data.

19. The computing system of claim 15, wherein the one or more processors are further configured to:
input, into the LLM, the future data to be classified by the LLM;
receive, from the LLM, the future plurality of classification values classifying the future data, wherein each future classification value of the future plurality of classification values includes an associated probability representing a likelihood that each future classification value is a valid output;
order the future plurality of classification values in descending order; and
determine the cutoff for the future plurality of classification values based on the quantile score; and
output, to a graphical user interface (GUI), a subset of the future plurality of classification values from a highest probability to the cutoff, for display to a user.

20. The computing system of claim 15, wherein the one or more processors are further configured to, re-compute the quantile score at predetermined intervals using updated calibration data.

* * * * *